(12) United States Patent
Burns (10) Patent No.: US 8,845,565 B1
(45) Date of Patent: Sep. 30, 2014

(54) ARM SLING NECK CUSHION KIT

(71) Applicant: B. Rodney Burns, Port St. Lucie, FL (US)

(72) Inventor: B. Rodney Burns, Port St. Lucie, FL (US)

( * ) Notice: Subject to any disclaimer, the term of this patent is extended or adjusted under 35 U.S.C. 154(b) by 0 days.

(21) Appl. No.: 13/656,324

(22) Filed: Oct. 19, 2012

(51) Int. Cl.
*A61F 5/00* (2006.01)

(52) U.S. Cl.
USPC .................................. 602/4; 602/5

(58) Field of Classification Search
USPC .............................. 602/4–5, 19; 128/878–879
See application file for complete search history.

(56) References Cited

U.S. PATENT DOCUMENTS

| | | | |
|---|---|---|---|
| 2,807,261 A * | 9/1957 | Strinden | 602/4 |
| 3,554,194 A | 1/1971 | Johnson | |
| 4,572,172 A * | 2/1986 | Williams | 602/4 |
| 4,716,895 A | 1/1988 | Marques et al. | |
| 4,733,658 A | 3/1988 | Ruthven, Jr. | |
| 5,334,132 A | 8/1994 | Burkhead | |
| 5,746,705 A * | 5/1998 | Sheppard | 602/5 |
| 6,976,971 B2 * | 12/2005 | Scudere | 602/4 |
| 7,563,236 B2 | 7/2009 | Kazmierczak et al. | |
| 2006/0013976 A1 | 1/2006 | Leiss | |
| 2008/0228116 A1 * | 9/2008 | Walker | 602/4 |
| 2011/0213282 A1 | 9/2011 | Cortese | |

\* cited by examiner

*Primary Examiner* — Michael A. Brown
(74) *Attorney, Agent, or Firm* — Richard L. Miller (57) ABSTRACT

A cushion that cushions the neck and shoulder of a user of a sling with a strap by being selectively secured anywhere along, and over, the strap of the sling so as to be positioned on the strap of the sling at the neck and shoulder of the user. The cushion includes an inner tube and an outer covering. The inner tube receives the strap of the sling to cushion the neck and shoulder of the user of the sling by being selectively secured anywhere along, and over, the strap of the sling so as to be positioned on the strap of the sling at the neck and shoulder of the user. The outer covering receives, and is replaceable relative to, the inner tube.

25 Claims, 6 Drawing Sheets

ARM SLING NECK CUSHION KIT

1. BACKGROUND OF THE INVENTION

A. Field of the Invention

The embodiments of the present invention relate to a sling cushion, and more particularly, the embodiments of the present invention relate to a cushion for cushioning the neck and shoulder of a user of a sling with a strap by being selectively secured anywhere along, and over, the strap of the sling so as to be positioned on the strap of the sling at the neck and shoulder of the user.

B. Description of the Prior Art

Numerous innovations for slings have been provided in the prior art, which will be described below in chronological order to show advancement in the art, and which are incorporated in their entirety herein by reference thereto. Even though these innovations may be suitable for the specific individual purposes to which they address, nevertheless, they differ from the present invention in that they do not teach a cushion for cushioning the neck and shoulder of a user of a sling with a strap by being selectively secured anywhere along, and over, the strap of the sling so as to be positioned on the strap of the sling at the neck and shoulder of the user, (1) U.S. Pat. No. 3,554,194 to Johnson.

U.S. Pat. No. 3,554,194—issued to Johnson on Jan. 12, 1971 in U.S. class 602 and subclass 4—teaches an arm sling including upper and lower loop or strap portions joined together to form a generally figure-eight configuration. The upper loop includes a padding including a plastic foam material encased within a fabric stockinet. The padding is adapted to bear against the nape of the patient's neck. The lower loop includes a padding of plastic foam material encased within a fabric stockinet. A pair of fabric straps are provided on the lower loop padding, and threadedly receive the lower strap portion to retain the lower padding in adjustable position therealong. A buckle is provided for adjusting the length of both the upper and lower loop strap portions.

(2) U.S. Pat. No. 4,716,895 to Marques et al.

U.S. Pat. No. 4,716,895—issued to Marques et al. on Jan. 5, 1988 in U.S. class 602 and subclass 4—teaches a sling for support of the arm, which includes an elongated cloth body having a relatively wide central region and relatively narrow end regions, and further having an arm extending outwardly from adjacent the central region. The body is mounted on one shoulder and supports the opposite arm without the need for any separate arm-containing pouch or pocket. Hook and loop fasteners are provided to secure the ends of the body to each other, and to secure the arm to the body.

(3) U.S. Pat. No. 4,733,658 to Ruthven, Jr.

U.S. Pat. No. 4,733,658—issued to Ruthven, Jr. on Mar. 29, 1988 in U.S. class 602 and subclass 4—teaches a one-piece pad of a generally L-shape provides a reversible sling. The pad is formed with a head-receiving opening, and includes on each of its sides, a plurality of attachment apparatus. A two-part folding action forms a sling for either arm, wrist, or hand. The sling immobilizes the injured arm, wrist, or hand in an upwardly inclined position above the heart, and also provides a comfortable elbow support.

(4) U.S. Pat. No. 5,334,132 to Burkhead.

U.S. Pat. No. 5,334,132—issued to Burkhead on Aug. 2, 1994 in U.S. class 602 and subclass 4—teaches an arm sling that includes a forearm support section having a resealable opening in a bottom panel for permitting exercise, and flexure and extension of a patient's forearm without removing the sling harness from the patient. A splint pocket is also provided for housing a removable splint for supporting the patient's hand in a neutral position. An external pocket encloses a foam cushion for conforming engagement with the patient's waist thus providing an abduction effect.

(5) United States Patent Application Publication Number 2006/0013976 to Leiss.

United States Patent Application Publication Number 2006/0013976—published to Leiss on Jan. 19, 2006 in U.S. class 428 and subclass 36.1—teaches a neck protector that is a cylindrical-shaped tube made of soft and thick fleece fabric. The dimensions are approximately 20" long with a 5½" circumference. The neck protector is for people who are wearing arm slings, typically after a broken arm or shoulder surgery. The weight of the arm puts a tremendous amount of pressure on the strap of the sling that has a tendency to rub and dig into the user's neck skin. This in turn can become painful and irritating to the user. The neck protector creates a soft cushion around the strap, thereby protecting the skin from harm. The neck protector easily slides over the strap portion of the arm sling. The user then adjusts the neck protector to a comfortable position around the back of the neck.

(6) U.S. Pat. No. 7,563,236 to Kazmierczak et al.

U.S. Pat. No. 7,563,236—issued to Kazmierczak et al. on Jul. 21, 2009 in U.S. class 602 and subclass 4—teaches a shoulder sling for the treatment of, for example, gleno-humeral dislocations and subluxations, capsular shifts, postoperative rotator cuff repair, postoperative Bankart procedures, and soft tissue strains and repairs. The sling includes a support pillow that abuts the wearer's torso, and a pouch that receives the wearer's arm. A plurality of straps suspend the pillow and pouch from the wearer's non-treatment shoulder. One of the straps prevents the pillow from shifting relative to the user, thus securely maintaining the wearer's arm at desired angles of abduction and external rotation. The pillow further includes an attached exercise grip and an indicator line that aids a physician in properly fitting the sling to the wearer.

(7) United States Patent Application Publication Number 2011/0213282 to Cortese.

United States Patent Application Publication Number 2011/0213282—published to Cortese on Sep. 1, 2011 in U.S. class 602 and subclass 4—teaches an arm sling having broad supporting area on the shoulder of the injured side supports the weight of the upper and lower arm and allows mobility of the upper arm and elbow. The other shoulder from which the non-injured arm depends bears no weight of the supported arm.

It is apparent that numerous innovations for slings have been provided in the prior art, which are adapted to be used. Furthermore, even though these innovations may be suitable for the specific individual purposes to which they address, nevertheless, they would not be suitable for the purposes of the embodiments of the present invention as heretofore described, namely, a cushion for cushioning the neck and shoulder of a user of a sling with a strap by being selectively secured anywhere along, and over, the strap of the sling so as to be positioned on the strap of the sling at the neck and shoulder of the user.

2. SUMMARY OF THE INVENTION

Thus, an object of the embodiments of the present invention is to provide a cushion for cushioning the neck and shoulder of a user of a sling with a strap by being selectively secured anywhere along, and over, the strap of the sling so as to be positioned on the strap of the sling at the neck and shoulder of the user, which avoids the disadvantages of the prior art.

Briefly stated, another object of the embodiments of the present invention is to provide a cushion that cushions the neck and shoulder of a user of a sling with a strap by being selectively secured anywhere along, and over, the strap of the sling so as to be positioned on the strap of the sling at the neck and shoulder of the user. The cushion includes an inner tube and an outer covering. The inner tube receives the strap of the sling to cushion the neck and shoulder of the user of the sling by being selectively secured anywhere along, and over, the strap of the sling so as to be positioned on the strap of the sling at the neck and shoulder of the user. The outer covering receives, and is replaceable relative to, the inner tube.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying figures of the drawing.

3. BRIEF DESCRIPTION OF THE FIGURES OF THE DRAWING

The figures of the drawing are briefly described as follows.

4. LIST OF REFERENCE NUMERALS UTILIZED IN THE FIGURES OF THE DRAWING

A. Introductory.

10 cushion of embodiments of present invention for cushioning neck 12 and shoulder 14 of user 16 of sling 18 with strap 20 by being selectively secured anywhere along, and over, strap 20 of sling 18 so as to be positioned on strap 20 of sling 18 at neck 12 and shoulder 14 of user 16

12 neck of user 16

14 shoulder of user 16

16 user

18 sling

20 strap of sling 18

B. Overall Configuration of Cushion 10.

22 inner tube for cushioning neck 12 and shoulder 14 of user 16 of sling 18 by being selectively secured anywhere along, and over, strap 20 of sling 18 so as to be positioned on strap 20 of sling 18 at neck 12 and shoulder 14 of user 16

24 outer covering

26 attaching apparatus

C. Specific Configuration of Inner Tube 22.

28 pair of ends of inner tube 22

30 through slit of inner tube 22

32 pair of opposing edges defining through slit 30 of inner tube 22

34 adhesive of inner tube 22 for adhering pair of opposing edges 32 defining through slit 30 of inner tube 22 to each other after inner tube 22 is secured anywhere along, and over, strap 20 of sling 18

36 release sheet of inner tube 22

D. Specific Configuration of Covering 24.

38 sleeve of covering 24

40 pair of ends of sleeve 38 of covering 24

E. Specific Configuration of Attaching Apparatus 26.

42 two pair of mating portions of hook and loop fastener strips of attaching apparatus 26

44 one portion of each pair of hook and loop fastener strips of two pair of mating portions of hook and loop fastener strips 42 of attaching apparatus 26

46 other portion of each pair of hook and loop fastener strips of two pair of mating portions of hook and loop fastener strips 42 of attaching apparatus 26 for attaching to strap 20 of sling 18

48 adhesive of two pair of mating portions of hook and loop fastener strips 42 of attaching apparatus 26

50 release sheets of two pair of mating portions of hook and loop fastener strips 42 of attaching apparatus 26

5. DETAILED DESCRIPTION OF THE PREFERRED EMBODIMENTS

A. Introductory.

Figure 1:
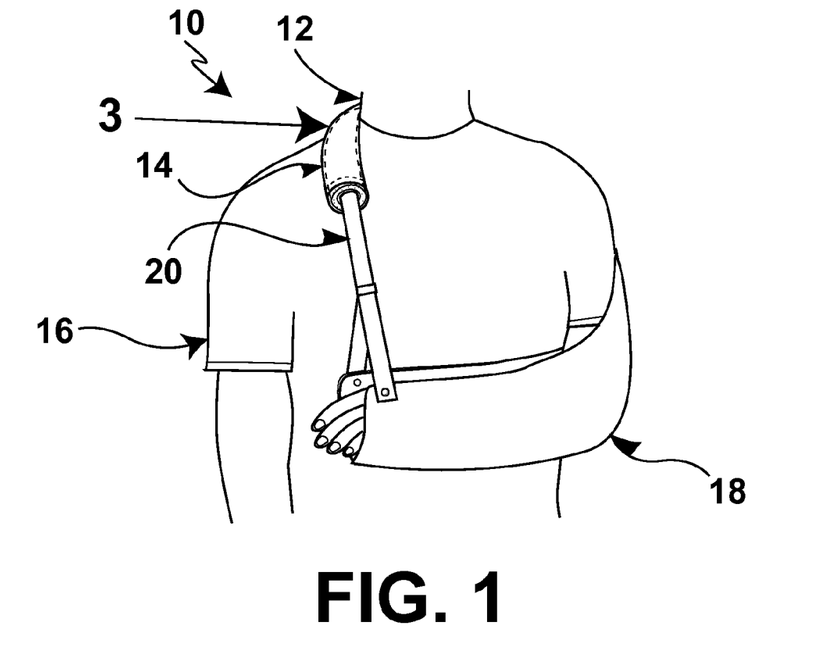
FIG. 1 is a diagrammatic perspective view of the cushion of the embodiments of the present invention cushioning the neck and shoulder of a user of a first type of sling with a strap by being selectively secured anywhere along, and over, the strap of the first type of sling so as to be positioned on the strap of the first type of sling at the neck and shoulder of the user.
Figure 2:
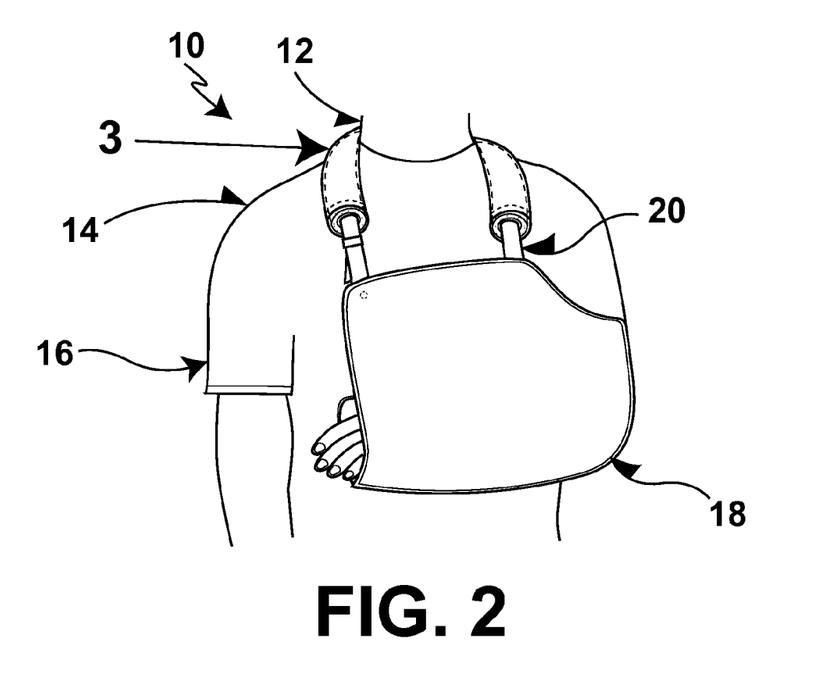
FIG. 2 is a diagrammatic perspective view of the cushion of the embodiments of the present invention cushioning the neck and shoulder of a user of a second type of sling with a strap by being selectively secured anywhere along, and over, the strap of the second type of sling so as to be positioned on the strap of the second type of sling at the neck and shoulder of the user.

Referring now to the figures, in which like numerals indicate like parts, and particularly to FIGS. 1 and 2, which are, respectively, a diagrammatic perspective view of the cushion of the embodiments of the present invention cushioning the neck and shoulder of a user of a first type of sling with a strap by being selectively secured anywhere along, and over, the strap of the first type of sling so as to be positioned on the strap of the first type of sling at the neck and shoulder of the user, and a diagrammatic perspective view of the cushion of the embodiments of the present invention cushioning the neck and shoulder of a user of a second type of sling with a strap by being selectively secured anywhere along, and over, the strap of the second type of sling so as to be positioned on the strap of the second type of sling at the neck and shoulder of the user, the cushion of the embodiments of the present invention is shown generally at 10 for cushioning the neck 12 and shoulder 14 of a user 16 of a sling 18 with a strap 20 by being selectively secured anywhere along, and over, the strap 20 of the sling 18 so as to be positioned on the strap 20 of the sling 18 at the neck 12 and shoulder 14 of the user 16.

B. The Overall Configuration of the Cushion 10.

Figure 3:
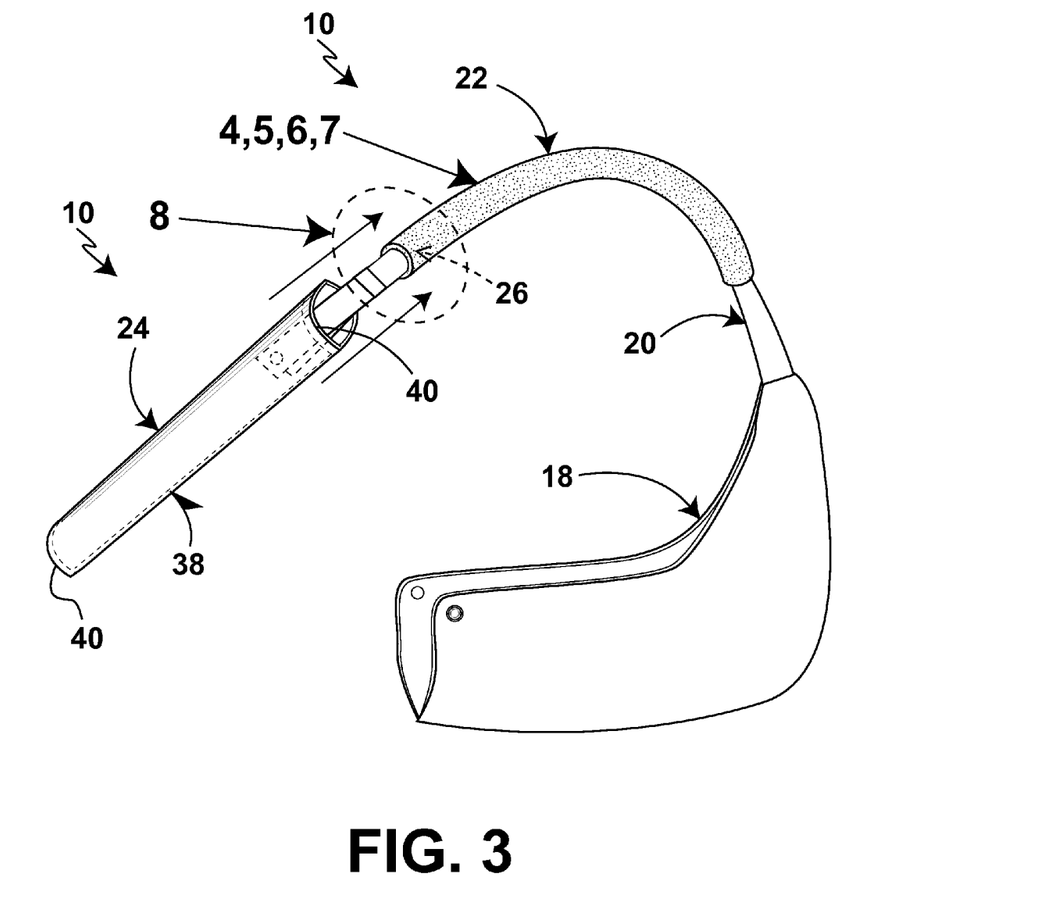
FIG. 3 is an enlarged diagrammatic perspective view of the cushion of the embodiments of the present invention identified by ARROW 3 in FIGS. 1 and 2.
Figure 4:
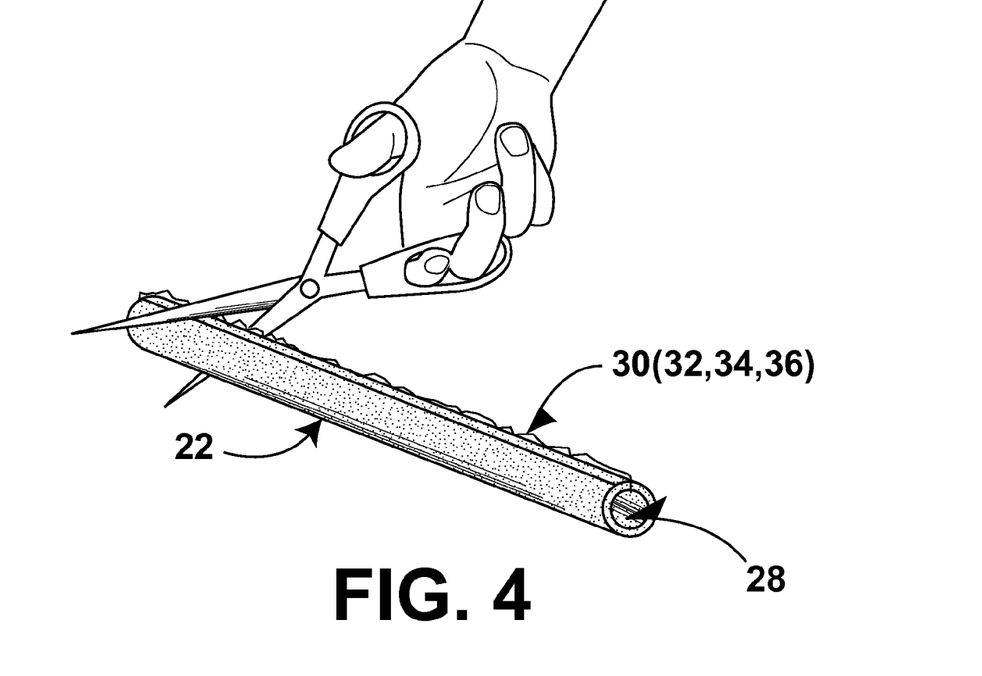
FIG. 4 is a diagrammatic perspective view of the inner tube of the cushion of the embodiments of the present invention identified by ARROW 4 in FIG. 3 and being cut to size.
Figure 5:
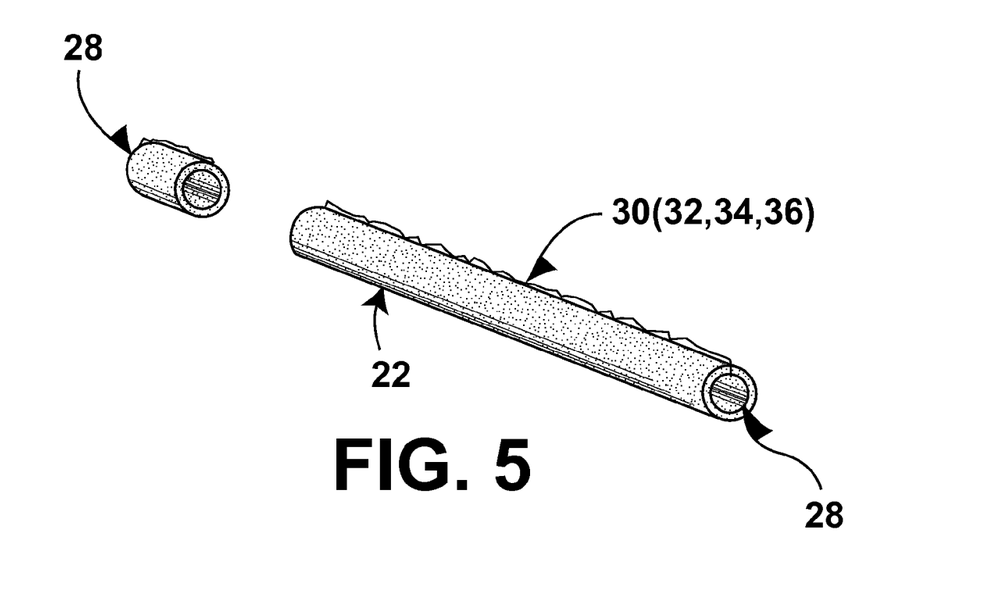
FIG. 5 is a diagrammatic perspective view of the inner tube of the cushion of the embodiments of the present invention identified by ARROW 5 in FIG. 3 cut to size and with a waste piece.
Figure 6:
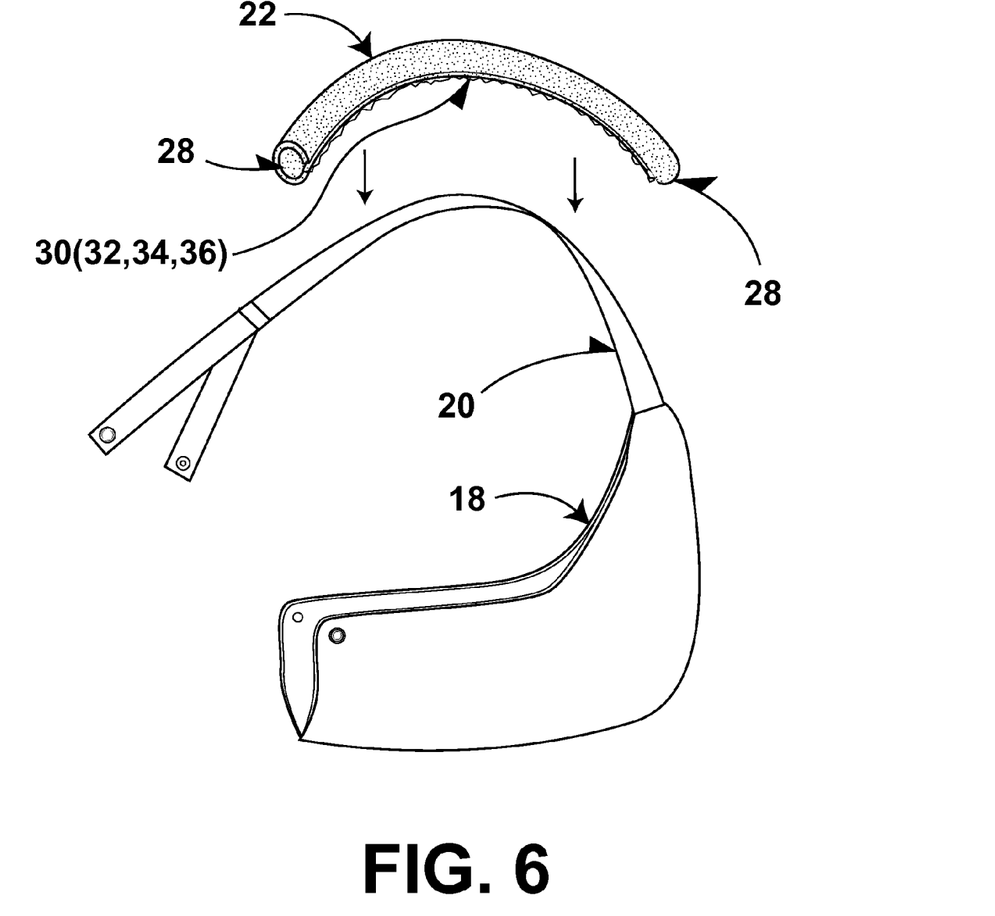
FIG. 6 is a diagrammatic perspective view of the inner tube of the cushion of the embodiments of the present invention identified by ARROW 6 in FIG. 3 being placed on a strap of a sling.
Figure 7:
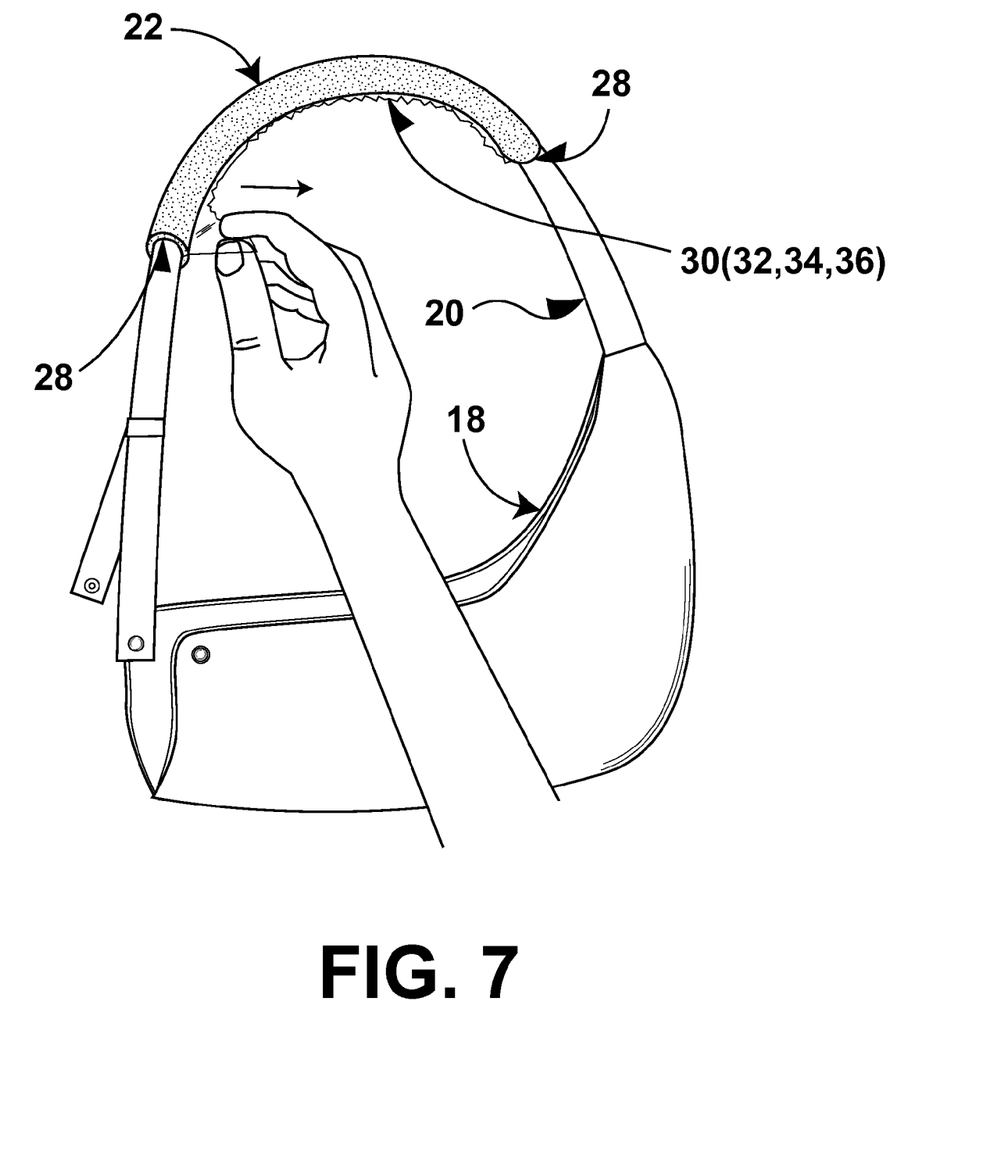
FIG. 7 is a diagrammatic perspective view of the inner tube of the cushion of the embodiments of the present invention identified by ARROW 7 in FIG. 3 on a strap of a sling and being adhered thereto.

The overall configuration of the cushion 10 can best be seen in FIG. 3, which is an enlarged diagrammatic perspective view of the cushion of the embodiments of the present invention identified by ARROW 3 in FIGS. 1 and 2, and as such, will be discussed with reference thereto.

The cushion 10 comprises an inner tube 22 and an outer covering 24. The inner tube 22 is for receiving the strap 20 of the sling 18 for cushioning the neck 12 and shoulder 14 of the user 16 of the sling 18 by being selectively secured anywhere along, and over, the strap 20 of the sling 18 so as to be positioned on the strap 20 of the sling 18 at the neck 12 and shoulder 14 of the user 16. The outer covering 24 receives, and is replaceable relative to, the inner tube 22.

The cushion 10 further comprises an attaching apparatus 26.

The attaching apparatus 26 is attached to, and within, the inner tube 22, and is for attaching to the strap 20 of the sling 18 so as to allow the attaching apparatus 26 to replaceably attach the cushion 10 to the strap 20 of the sling 18 so as to allow the cushion 10 to be positioned on the strap 20 of the sling 18 at the neck 12 and shoulder 14 of the user 16.

C. The Specific Configuration of the Inner Tube 22.

The specific configuration of the inner tube 22 can best be seen in FIGS. 4, 5, 6, and 7, which are, respectively, a diagrammatic perspective view of the inner tube of the cushion of the embodiments of the present invention identified by ARROW 4 in FIG. 3 and being cut to size, a diagrammatic perspective view of the inner tube of the cushion of the embodiments of the present invention identified by ARROW 5 in FIG. 3 cut to size and with a waste piece, a diagrammatic perspective view of the inner tube of the cushion of the embodiments of the present invention identified by ARROW 6 in FIG. 3 being placed on the strap of the sling, and a diagrammatic perspective view of the inner tube of the cushion of the embodiments of the present invention identified by ARROW 7 in FIG. 3 on the strap of the sling and being adhered thereto, and as such, will be discussed with reference thereto.

The inner tube 22 is slender, elongated, flexible, readily cuttable, cushiony for cushioning the neck 12 and shoulder 14 of the user 16 of the sling 18, and has a pair of ends 28.

The inner tube 22 further has a through slit 30.

The through slit 30 of the inner tube 22 extends axially therealong, from one end 28 of the inner tube 22 to the other end 28 of the inner tube 22 so as to allow the inner tube 22 to be bent open and secured anywhere along, and over, the strap 20 of the sling 18 so as to be positioned on the strap 20 of the sling 18 at the neck 12 and shoulder 14 of the user 16.

The through slit 30 of the inner tube 22 is defined by a pair of opposing edges 32.

The inner tube 22 further has an adhesive 34.

The adhesive 34 of the inner tube 22 is disposed along the pair of opposing edges 32 defining the through slit 30 of the inner tube 22, and is for adhering the pair of opposing edges 32 defining the through slit 30 of the inner tube 22 to each other after the inner tube 22 is positioned anywhere along, and over, the strap 20 of the sling 18.

The inner tube 22 further has a release sheet 36.

The release sheet 36 of the inner tube 22 is disposed between, and contacts, the adhesive 34 of the inner tube 22 that is on the pair of opposing edges 32 defining the through slit 30 of the inner tube 22 before the pair of opposing edges 32 defining the through slit 30 of the inner tube 22 are adhered to each other, and when the inner tube 22 receives the strap 20 of the sling 18 and the pair of opposing edges 32 defining the through slit 30 of the inner tube 22 are to be adhered to each other, the release sheet 36 of the inner tube 22 is removed exposing the adhesive 34 of the inner tube 22 that is on the pair of opposing edges 32 defining the through slit 30 of the inner tube 22 and adhering the pair of opposing edges 32 defining the through slit 30 of the inner tube 22 to each other.

D. The Specific Configuration of the Covering 24.

The specific configuration of the covering 24 can best be seen in FIG. 3, which is, again, an enlarged diagrammatic perspective view of the cushion of the embodiments of the present invention identified by ARROW 3 in FIGS. 1 and 2, and as such, will be discussed with reference thereto.

The covering 24 comprises a sleeve 38.

The sleeve 38 of the covering 24 has a pair of ends 40. The pair of ends 40 of the sleeve 38 of the covering 24 are open so as to allow the sleeve 38 of the covering 24 to coaxially receive the inner tube 22 through the pair of ends 40 of the sleeve 38 of the covering 24.

The sleeve 38 of the covering 24 is made of a washable pillow case material for being periodically laundered since the sleeve 38 of the covering 24 comes in contact with the neck 12 and the shoulder 14 of the user 16 during use of the cushion 10.

The washable pillow case material of the sleeve 38 of the covering 24 is, preferably, made of cloth or silk, but is not limited to that.

E. The Specific Configuration of the Attaching Apparatus 26.

Figure 8:
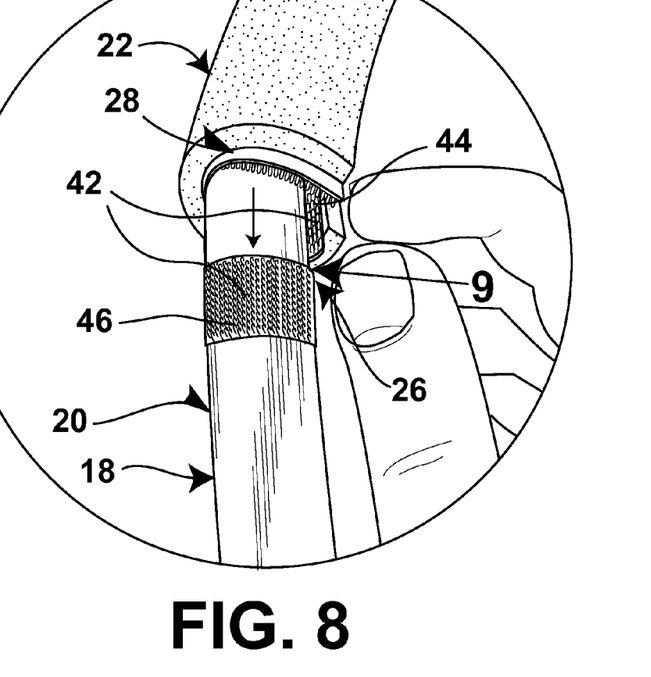
FIG. 8 is an enlarged diagrammatic perspective view of the area generally enclosed by the dotted circle identified by ARROW 8 in FIG. 3 of the attaching apparatus of the cushion of the embodiments of the present invention.
Figure 9:
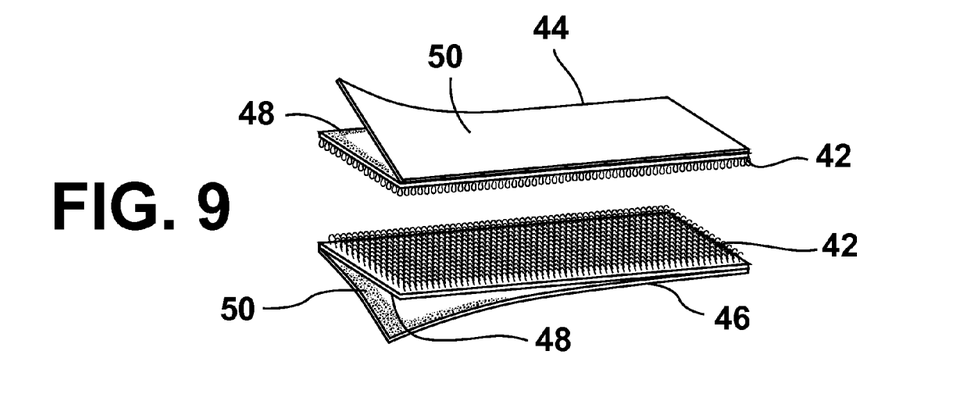
FIG. 9 is an enlarged and exploded perspective view of a mating pair of hook and loop fasteners of the attaching apparatus of the cushion of the embodiments of the present invention identified by ARROW 9 in FIG. 8.

The specific configuration of the attaching apparatus 26 can best be seen in FIGS. 8 and 9, which are, respectively, an enlarged diagrammatic perspective view of the area generally enclosed by the dotted circle identified by ARROW 8 in FIG. 3 of the attaching apparatus of the cushion of the embodiments of the present invention, and an enlarged and exploded perspective view of a mating pair of hook and loop fasteners of the attaching apparatus of the cushion of the embodiments of the present invention identified by ARROW 9 in FIG. 8, and as such, will be discussed with reference thereto.

The attaching apparatus 26 comprises two pair of mating portions of hook and loop fastener strips 42.

The two pair of mating portions of hook and loop fastener strips 42 of the attaching apparatus 26 are attached to, and are within, the pair of ends 28 of the inner tube 22, respectively, and are for replaceably attaching to the strap 20 of the sling 18.

One portion 44 of each pair of hook and loop fastener strips 42 of the attaching apparatus 26 are attached to, and are within, the pair of ends 28 of the inner tube 22, respectively, while the other portion 46 of each pair of hook and loop fastener strips 42 of the attaching apparatus 26 are for replaceably attaching to the strap 20 of the sling 18 so as to allow the cushion 10 to be secured anywhere along the strap 20 of the sling 18 so as to be positioned on the strap 20 of the sling 18 at the neck 12 and shoulder 14 of the user 16.

The one portion 44 of each pair of hook and loop fastener strips 42 of the attaching apparatus 26 and the other portion 46 of each pair of hook and loop fastener strips 42 of the attaching apparatus 26 comprise an adhesive 48.

The adhesive 48 of the two pair of mating portions of hook and loop fastener strips 42 of the attaching apparatus 26 extend therealong so as to attach the one portion 44 of each pair of hook and loop fastener strips 42 of the attaching apparatus 26 to the pair of ends 28 of the inner tube 22, respectively, and to replaceably attach the other portion 46 of each pair of hook and loop fastener strips 42 of the attaching apparatus 26 to the strap 20 of the sling 18 so as to allow the cushion 10 to be secured anywhere along the strap 20 of the sling 18 so as to be positioned on the strap 20 of the sling 18 at the neck 12 and shoulder 14 of the user 16.

The adhesive 48 used on the other portion 46 of each pair of hook and loop fastener strips 42 of the attaching apparatus 26 to replaceably attach the other portion 46 of each pair of hook and loop fastener strips 42 of the attaching apparatus 26 to the strap 20 of the sling 18 is a reuseable adhesive so as to allow the cushion 10 to be secured anywhere along the strap 20 of the sling 18 so as to be positioned on the strap 20 of the sling 18 at the neck 12 and shoulder 14 of the user 16.

The one portion 44 of each pair of hook and loop fastener strips 42 of the attaching apparatus 26 and the other portion 46 of each pair of hook and loop fastener strips 42 of the attaching apparatus 26 comprise release sheets 50.

F. Impressions.

It will be understood that each of the elements described above or two or more together may also find a useful application in other types of constructions differing from the types described above.

While the embodiments of the present invention have been illustrated and described as embodied in a cushion for cushioning the neck and shoulder of a user of a sling with a strap by being selectively secured anywhere along, and over, the strap of the sling so as to be positioned on the strap of the sling at the neck and shoulder of the user, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis, the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A cushion for cushioning the neck and shoulder of a user of a sling with a strap by being selectively secured anywhere along, and over, the strap of the sling so as to be positioned on the strap of the sling at the neck and shoulder of the user, comprising:
   a) an inner tube; and
   b) an outer covering;
   wherein said inner tube is for receiving the strap of the sling for cushioning the neck and shoulder of the user of the sling by being selectively secured anywhere along, and over, the strap of the sling so as to be positioned on the strap of the sling at the neck and shoulder of the user;
   wherein said outer covering receives said inner tube;
   wherein said outer covering is replaceable relative to said inner tube, further comprising an attaching apparatus;
   wherein said inner tube has a through slit;
   wherein said through slit of said inner tube is defined by a pair of opposing edges,
   wherein said inner tube has an adhesive; and
   wherein said adhesive of said inner tube is for adhering said pair of opposing edges defining said through slit of said inner tube to each other after said inner tube is positioned anywhere along, and over, the strap of the sling.

2. The cushion of claim 1, wherein said attaching apparatus is attached to said inner tube;
   wherein said attaching apparatus is within said inner tube; and
   wherein said attaching apparatus is for attaching to the strap of the sling so as to allow said attaching apparatus to replaceably attach said cushion to the strap of the sling so as to allow said cushion to be positioned on the strap of the sling at the neck and shoulder of the user.

3. The cushion of claim 1, wherein said inner tube is slender.

4. The cushion of claim 1, wherein said inner tube is elongated.

5. The cushion of claim 1, wherein said inner tube is flexible.

6. The cushion of claim 1, wherein said inner tube is readily cuttable.

7. The cushion of claim 1, wherein said inner tube is cushiony for cushioning the neck and shoulder of the user of the sling.

8. The cushion of claim 1, wherein said through slit of said inner tube extends axially therealong.

9. The cushion of claim 1, wherein said inner tube has a pair of ends; and
   wherein said through slit of said inner tube extends from one end of said inner tube to the other end of said inner tube so as to allow said inner tube to be bent open and secured anywhere along, and over, the strap of the sling so as to be positioned on the strap of the sling at the neck and shoulder of the user.

10. The cushion of claim 9, wherein said attaching apparatus comprises two pair of mating portions of hook and loop fastener strips.

11. The cushion of claim 10, wherein said two pair of mating portions of hook and loop fastener strips of said attaching apparatus are attached to said pair of ends of said inner tube, respectively; and
   wherein said two pair of mating portions of hook and loop fastener strips of said attaching apparatus are for replaceably attaching to the strap of the sling.

12. The cushion of claim 10, wherein said two pair of mating portions of hook and loop fastener strips of said attaching apparatus are within said pair of ends of said inner tube, respectively.

13. The cushion of claim 10, wherein one portion of each pair of hook and loop fastener strips of said attaching apparatus are attached to, and are within, said pair of ends of said inner tube, respectively, while the other portion of each pair of hook and loop fastener strips of said attaching apparatus are for replaceably attaching to the strap of the sling so as to allow said cushion to be secured anywhere along the strap of the sling so as to be positioned on the strap of the sling at the neck and shoulder of the user.

14. The cushion of claim 13, wherein said one portion of each pair of hook and loop fastener strips of said attaching apparatus and said other portion of each pair of hook and loop fastener strips of said attaching apparatus comprise an adhesive.

15. The cushion of claim 14, wherein said adhesive of said two pair of mating portions of hook and loop fastener strips of said attaching apparatus extend therealong so as to attach said one portion of each pair of hook and loop fastener strips of said attaching apparatus to said pair of ends of said inner tube, respectively, and to replaceably attach said other portion of each pair of hook and loop fastener strips of said attaching apparatus to the strap of the sling so as to allow said cushion to be secured anywhere along the strap of the sling so as to be positioned on the strap of the sling at the neck and shoulder of the user.

16. The cushion of claim 15, wherein said adhesive used on said other portion of each pair of hook and loop fastener strips of said attaching apparatus to replaceably attach said other portion of each pair of hook and loop fastener strips of said attaching apparatus to the strap of the sling is a reuseable adhesive so as to allow said cushion to be secured anywhere along the strap of the sling so as to be positioned on the strap of the sling at the neck and shoulder of the user.

17. The cushion of claim 15, wherein said one portion of each pair of hook and loop fastener strips of said attaching apparatus and said other portion of each pair of hook and loop fastener strips of said attaching apparatus comprise release sheets.

18. The cushion of claim 1, wherein said adhesive of said inner tube is disposed along said pair of opposing edges defining said through slit of said inner tube.

19. The cushion of claim 1, wherein said inner tube has a release sheet.

20. The cushion of claim 19, wherein said release sheet of said inner tube is disposed between, and contacts, said adhesive of said inner tube that is on said pair of opposing edges defining said through slit of said inner tube before said pair of opposing edges defining said through slit of said inner tube are adhered to each other; and wherein when said inner tube receives the strap of the sling and said pair of opposing edges defining said through slit of said inner tube are to be adhered to each other, said release sheet of said inner tube is removed exposing said adhesive of said inner tube that is on said pair of opposing edges defining said through slit of said inner tube and adhering said pair of opposing edges defining said through slit of said inner tube to each other.

21. The cushion of claim 1, wherein said covering comprises a sleeve.

22. The cushion of claim 21, wherein said sleeve of said covering has a pair of ends; and wherein said pair of ends of said sleeve of said covering are open so as to allow said sleeve of said covering to coaxially receive said inner tube through said pair of ends of said sleeve of said covering.

23. The cushion of claim 21, wherein said sleeve of said covering is made of a washable pillow case material for being periodically laundered since said sleeve of said covering comes in contact with the neck and the shoulder of the user during use of said cushion.

24. The cushion of claim 23, wherein said washable pillow case material of said sleeve of said covering is made of cloth.

25. The cushion of claim 23, wherein said washable pillow case material of said sleeve of said covering is made of silk.

* * * * *